United States Patent
Shah et al.

(10) Patent No.: US 8,801,723 B2
(45) Date of Patent: Aug. 12, 2014

(54) MINIMALLY INVASIVE SURGICAL APPLICATOR

(71) Applicant: Insight Surgical Instruments, LLC, San Francisco, CA (US)

(72) Inventors: Ajay Shah, San Francisco, CA (US); Jeffrey Manassero, Newport Beach, CA (US); Elizabeth Orwin, Upland, CA (US); Vincent Pai, Walnut, CA (US); Anne Jensen, Lexington, KY (US); Matthew Phillips, Salem, OR (US); Timothy Challener, Raleigh, NC (US); Cassie Nguyen, Phoenix, AZ (US); Kristen Schunter, Fort Collins, CO (US)

(73) Assignee: Insight Surgical Instruments, LLC, San Francisco, CA (US)

( * ) Notice: Subject to any disclaimer, the term of this patent is extended or adjusted under 35 U.S.C. 154(b) by 0 days.

(21) Appl. No.: 14/071,938

(22) Filed: Nov. 5, 2013

(65) Prior Publication Data

US 2014/0058399 A1 Feb. 27, 2014

Related U.S. Application Data

(63) Continuation of application No. 13/741,786, filed on Jan. 15, 2013, now Pat. No. 8,603,097, which is a continuation of application No. PCT/US2012/036081, filed on May 2, 2012.

(60) Provisional application No. 61/481,511, filed on May 2, 2011.

(51) Int. Cl.
*A61B 17/58* (2006.01)
*A61B 17/60* (2006.01)
*A61F 2/00* (2006.01)

(52) U.S. Cl.
USPC .......................................................... 606/93

(58) Field of Classification Search
USPC .......................................................... 606/93
See application file for complete search history.

(56) References Cited

U.S. PATENT DOCUMENTS

| | | | |
|---|---|---|---|
| 3,698,394 A | 10/1972 | Piper et al. | |
| 4,265,618 A * | 5/1981 | Herskovitz et al. | 433/32 |
| 4,457,712 A * | 7/1984 | Dragan | 433/90 |
| 5,569,213 A | 10/1996 | Humphrey | |
| 6,436,143 B1 * | 8/2002 | Ross et al. | 623/17.16 |
| 6,752,789 B2 | 6/2004 | Duchon et al. | |
| 7,448,867 B2 * | 11/2008 | Aloise et al. | 433/81 |

OTHER PUBLICATIONS

International Search Report for International Application.: PCT/US2012/036081 dated Aug. 24, 2012.

\* cited by examiner

*Primary Examiner* — Sameh Boles
(74) *Attorney, Agent, or Firm* — DT Ward, PC; Donna T. Ward

(57) ABSTRACT

The present invention provides a minimally invasive surgical applicator device. The device is useful in the application of bone wax during surgical procedures to halt or reduce bone bleeding. The device may be sterilized for re-use or may be made disposable.

22 Claims, 18 Drawing Sheets

A.

B.

MINIMALLY INVASIVE SURGICAL APPLICATOR

CROSS REFERENCE TO RELATED APPLICATIONS

This patent application is a continuation of U.S. application Ser. No. 13/741,786 filed Jan. 15, 2013, which is a continuation of International Application PCT/US2012/036081 filed on May 2, 2012 which claims the benefit of U.S. Provisional Patent Application No. 61/481,511 filed on May 2, 2011, the contents and teachings each of which are hereby incorporated by reference in their entirety.

FIELD OF THE INVENTION

The present invention provides a minimally invasive applicator device for use in surgical settings. The applicator may be used to apply therapeutic or surgical materials, preferably at an elevated temperature. Such materials include, for example, sealants, adhesives, therapeutic compositions such as creams, ointments and gels, structural components such as bone, hydroxyapatite and/or bone wax, particularly malleable materials and those having temperature dependent phase changes. The device may be sterilized for re-use or may be made disposable.

BACKGROUND OF THE INVENTION

Versatility in surgical instruments, especially those used to conduct minimally invasive procedures is of greater importance with recent advancements in the field. Minimally invasive surgical procedures are typically conducted through small ports and are characterized as endoscopic, laparoscopic, thoracoscopic, and the like. Such procedures require, not only that the instruments be precise but that the same instrument performs multiple functions.

Additionally, as surgical techniques become more advanced, surgery is increasingly being performed through smaller exposures. Minimally invasive and robotic surgeries are increasing in numbers across surgical specialties, such as neurosurgery, orthopedic surgery, cardiac surgery, thoracic surgery, and otolaryngology. Surgery on many deep portions of the body can now be performed through micro-incisions, small tubular ports, and robotic arms resulting in better surgical results, fewer complications, less pain, quicker recovery times, and decreased rates of infection. Surgical visualization and precision are even more important in these surgeries. Consequently, a device which can be adapted to administer any number of materials or substances to a specific location of the patient's body both quickly and easily will be preferred over a collection of instruments that perform the same tasks.

It is appreciated that the instruments and their payload be compatible with the surgical field. For example, it is often critical that the temperature of the instruments used be similar to the temperature of the conditional surgical setting, whether very low as in organ transplantation or at normal body temperature or at slightly above room temperature. In order to achieve the foregoing, it is often necessary to warm either the instrument or the materials the instruments will deliver. Ideally the instrument would be designed to warm the materials being used either prior to or during administration or contact with the patient.

The present invention provides such a surgical instrument. In one embodiment the present invention finds utility in the application of bone wax during orthopedic surgery.

A principal requirement of all surgery is hemostasis. When living tissue is incised, bleeding results and without hemostasis, blood loss can result in significant and life threatening anemia which may require blood product transfusion and intravenous vasopressor medications to prevent complications such as myocardial infarction, cerebral ischemia, and cardiac arrest. Additionally, bleeding obscures the surgical field which is of primary concern when surgery is performed though minimal access ports and under microsurgical magnification. Impaired visualization from bleeding can dramatically affect the accuracy, efficiency, safety, and speed of a surgical operation. At the conclusion of the operation, hemostasis is necessary to prevent post-surgical hematoma formation that can cause neurological deficit (temporary or permanent), pain, anemia, wound breakdown, and infection; all which can require re-operation, cause significant morbidity & mortality, and lead to ballooning health care expenses.

Traditionally, hemostasis is obtained during surgery of soft tissues via a combination of electrocautery and ligature. However, bone bleeding cannot be electrocauterized nor ligated. Instead, it requires application of bone wax.

Bone is a living and highly vascular tissue. When bone is incised, bleeding can be significant. Bleeding from bone mainly originates from venous channels located in the trabecular network. In operations involving the cranium, spine, chest, or other bone structure, bone wax is typically smeared along the bleeding surface to achieve hemostasis. Commonly, the instrument used to apply the bone wax is the surgeon's index finger or a blunt surgical dissector. The wax is softened to allow for it to be rolled into a ball and applied on the tip of a surgical instrument where it is then smeared along the bleeding surface. This intercalates the wax into the trabecular surface where it provides hemostasis.

The current methods for bone wax application are crude, imprecise, and often ineffective. For example, during microsurgery of the spine, millimeter scale precision is typically required for surgical maneuvers and instruments near the spinal cord and nerve roots. There is no margin of error near the spinal cord as the patient's neurological function can be permanently compromised by accidental and uncontrolled movements around the spinal cord or brain with less force than it takes to strike a key on a keyboard. Using one's finger does not provide the accuracy and control necessary to apply wax in these delicate locations.

Finally, it is known that application of bone wax impairs osteogenesis and can contribute to increased rates of infection. While it is necessary to obtain hemostasis, improved precision in application should decrease the amount of wax necessary to achieve the same result.

Bone wax is a hemostatic agent which has been used over the past century to prevent bleeding. Today, it is mostly comprised of beeswax (72.63%), and is softened with paraffin wax (14.87%) and isopropyl palmitate (12.5%). Bone wax functions by creating a physical barrier that blocks blood flow (ETHICON Bone Wax; MSDS No. Ethicon 151B; Dec. 27, 1989).

Although bone wax is widely accepted as a means to stop bleeding in bone, it has some significant disadvantages. Since bone wax is not biodegradable, it is not reabsorbed into the body. This unnatural barrier inhibits bone regeneration and increases risk of infection (Hoffmann, B., et al. "A New Biodegradable Bone Wax Substitute with the Potential to be used as a Bone Filling Material." *Journal of Materials Chemistry.* 17 (2007): 4028). As excess bone wax can be harmful to a patient's recovery, surgeons attempt to minimize its use. In fact, in procedures where bone fusion is critical, the use of bone wax is avoided altogether (Magyar, C. E., et al. "Ostene, A New Alkylene Oxide Copolymer Bone Hemostatic Material, does Not Inhibit Bone Healing." *Neurosurgery* 63.4 Suppl 2 (2008): 373.) Alternatives to bone wax, such as gelatin, microfibrillar collagen, and oxidized regenerated cellulose have been developed to address these negative properties, but bone wax remains the most widely used hemostatic agent (Schonauer, C., et al. "The use of Local Gents: Bone Wax, Gelatin, Collagen, Oxidized Cellulose." *Eur Spine J.* 13 (2004): S89).

The term minimally invasive surgery refers to any surgery that uses a smaller than traditional opening. These surgical procedures require very small skin and soft tissue openings, often only a few centimeters in diameter. In general, minimally invasive surgeries utilize a special retractor system that creates a port to the surgical field. Such retractor systems are typically 18-25 mm wide and 40-110 mm long, however, as the average size of an American person is growing, longer retractors are often needed.

The smaller incisions afforded by these methods have numerous benefits for the patient including smaller scars, less blood loss, shorter hospital stays, and faster recovery periods (Sasani et. al., 2010). The procedures also reduce trauma, lessen the potential for blood clots, and decrease costs associated with extended therapy (Rosenthal et. al., 1994).

Given the foregoing, there remains a critical need in the art for a specific, minimally invasive applicator device

SUMMARY OF THE INVENTION

The present invention embraces the design, construction, and testing of an applicator device capable of being used in minimally invasive procedures. The device or apparatus of the present invention is uniquely designed to deliver or administer therapeutic or surgical materials, preferably at an elevated temperature. Such materials include, for example, sealants, adhesives, therapeutic compositions such as creams, ointments and gels, structural components such as bone, hydroxyapatite and/or bone wax, and/or particularly malleable materials and those having temperature dependent phase changes.

As used herein, an "elevated temperature" refers to any temperature above a baseline temperature. It is contemplated that even room temperature could comprise an elevated temperature over the colder environment of a sterile surgical field which is below typical room temperature of approximately 25° C. Elevated temperature therefore may range from 20 to 50° C.

While the apparatus of the present invention may be employed to deliver any material or surgical substance (including therapeutic compounds and compositions) the apparatus will be described in detail in the context of use as an applicator for bone wax in the management of hemostasis.

The device of the present invention comprises four interconnected components or systems. These are the gripping means, the applicator system or tip, the wax loading system or mechanism, and a heating mechanism. Through an iterative design process, coupled with experimental testing, the device of the present invention comprises a spring-loaded hook mechanism for actuation of the device, a clover shaped tip with a slight upwards angle for the tip design, a positive thermal coefficient (PTC) heating element wrapped around the wax delivery tube (bayonet) for a heating element design, and an open slot for the wax loading. Each of these components and their equivalents is illustrated and described herein in detail.

DETAILED DESCRIPTION OF THE INVENTION

The present invention provides a minimally invasive applicator device for use in surgical settings. The applicator may be used to apply therapeutic or surgical materials, preferably at an elevated temperature. Such materials include, for example, sealants, adhesives, therapeutic compositions such as creams, ointments and gels, structural components such as bone, hydroxyapatite and/or bone wax, particularly malleable materials and those having temperature dependent phase changes.

The bone wax applicator device or apparatus of the present invention comprises at least an applicator body, a grip or trigger assembly, a heating assembly, and an extrusion rod, or wax extrusion rod in the exemplary embodiment described herein.

The grip or trigger assembly is an ergonomically friendly, squeezable handle which can be held with a single hand. Squeezing the handle ratchets the wax extrusion rod down the barrel of the bayonet, extruding the wax through the tip in a controllable and precise fashion. The bayonet features a heating element which warms the wax to optimize surgical application. The heating element is powered by a battery, although other power sources may be used. The heating assembly features an insulating layer outside the heating element to keep the outer temperature of the bayonet cool. The grip design also provides for a mechanical advantage, so that even if the heating element is turned off, the wax can be readily extruded from the device with a comfortable amount of force.

The wax is loaded in the open slot of the top of the grip, also called the wax loading chamber. According to the present invention, the apparatus may be manufactured with the wax or other surgical material pre-loaded or feature alternative loading ports described herein.

The bayonet is long and narrow with an external diameter of approximately 8 mm to allow it to easily fit down a minimally invasive surgical port as well as optimize the surgeon's field of vision.

According to the present invention, the bayonet may range from 10 to 30 cm in length.

The tip attached to, or formed at the end of, the bayonet is preferably rounded to aid in the spreading of wax across surfaces of cut bone.

According to the present invention, the central cavity of the bayonet has an internal diameter of between 0.1 cm and 1.0 cm and external diameter of between 0.5 and 1.5 cm. The internal diameter is preferably no larger than 8 mm in diameter. The present device allows for the application of bone wax to a depth of at least 10 cm to more than 30 cm. The device also allows for controlled quantities of bone wax to be delivered quickly and precisely to a variety of bone surface orientations, and with enough pressure to reliably achieve hemostasis.

Figure 1:
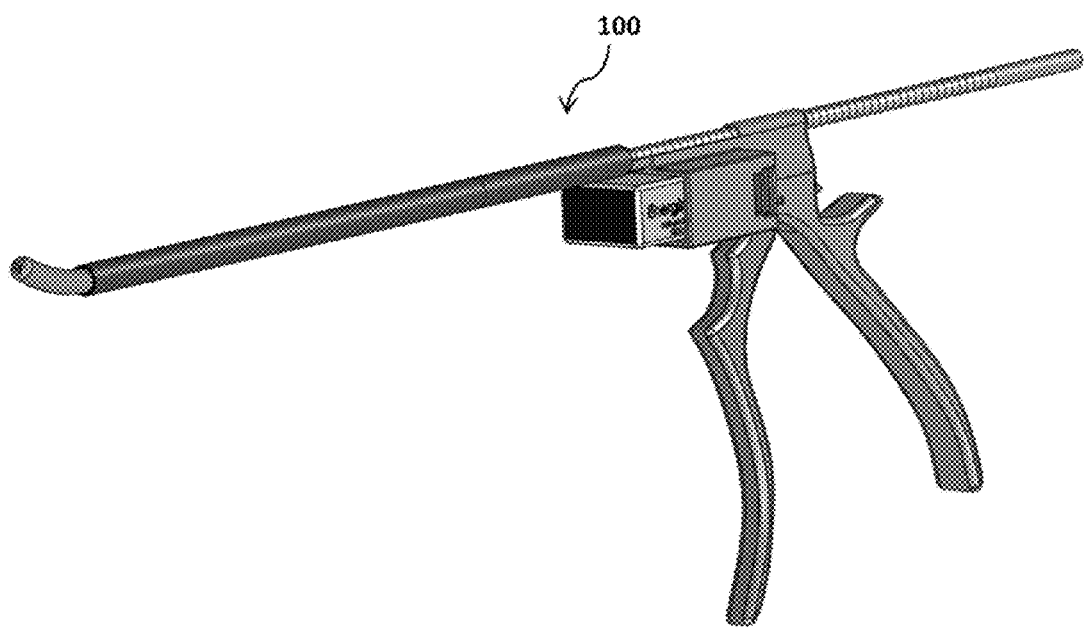
FIG. 1 illustrates a one embodiment of the bone wax applicator of the present invention.

Turning to the figures, FIG. 1 illustrates a one embodiment of the bone wax applicator 100 of the present invention. The device is shown with the extrusion rod engaged and having an angled tip.

Figure 2:
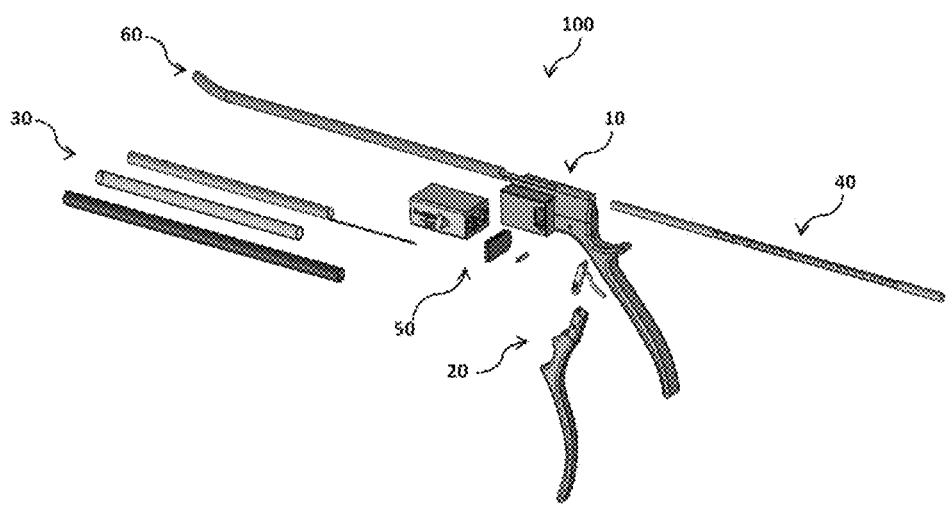
FIG. 2 illustrates the various component systems of the bone wax applicator. Shown in general detail are the applicator body, the grip or trigger assembly, the heating assembly, the wax extrusion rod, the heat source assembly, and the tip surface.

FIG. 2 illustrates the component systems of the bone wax applicator 100. Shown in general detail are the applicator body 10, the grip or trigger assembly 20, the heating assembly 30, the wax extrusion rod 40, the heat source assembly 50, and the tip surface 60. Each of these components will now be described in detail.

Figure 3:
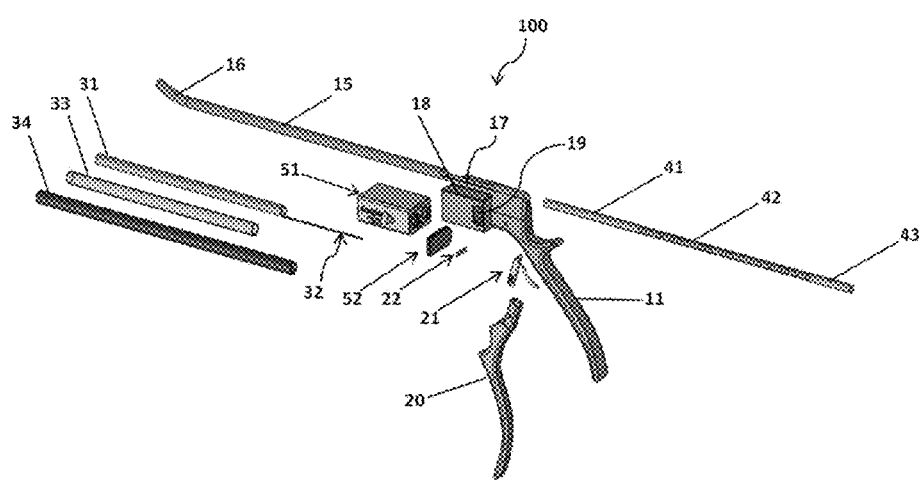
FIG. 3 illustrates details of the applicator body of the bone wax applicator of the invention.

Turning to FIG. 3, the applicator body 10 of the bone wax applicator of the invention 100 comprises the rear grip 11 (further detailed in FIG. 4), a wax delivery tube or bayonet 15 through which the bone wax travels for delivery to the site of administration, a tip 16, a wax loading chamber 17 shown in the figure with an open hatch design for receiving the bone wax and a battery housing 18.

The applicator body including the rear grip, bayonet, tip, wax loading chamber and battery housing may be machined, made, formed, molded or manufactured as one piece or in components which are assembled in a configuration as shown. For example, the battery housing may be manufactured separately from the applicator body and then attached or connected to the applicator body.

It is contemplated by the present invention that various types of tips may be employed in conjunction with the bone wax applicator and as such varying tip designs (discussed herein) may be made to be affixed, either temporarily or permanently, to the terminus of the bayonet. Tips may also be an integral part of the applicator body and therefore be made as part of the "one piece" design.

The length of the tip may vary from 0.5 cm to 5 cm. Tips may be straight, angled or curved.

In functioning, bone wax is inserted into the bone wax chamber 17 and pushed through the bayonet by the forward actuation of the wax extrusion rod 40. The wax extrusion rod comprises a first region, a second region and optionally a third region. The proximal end of the wax extrusion rod or first region represents the plunger region 41. It is this region which is inserted into the rear opening of the applicator body 10, and travels into and through the wax loading chamber 17 and inside the bayonet. This first region is connected immediately distal to a second region, the notched region 42 of the wax extrusion rod. The notched region is designed to engage a spring loaded hook 21 which is actuated by the movement of the front grip trigger assembly 20 (detailed in FIG. 5). The distal portion or optional third region of the wax extrusion rod 40 is the handle region 43. The handle region is utilized by the operator of the applicator to align or position the rod into the applicator body. Although not shown in the figure, the extrusion rod may contain a small hole passing perpendicularly and cross-wise through region three through which a ring or bar may be threaded to serve as a handle so the extrusion rod can be more easily retracted.

Both the applicator body and wax extrusion rod may be manufactured from aluminum, stainless steel or other suitable material.

Once wax has been inserted into the wax chamber 17 and the wax extrusion rod 40 inserted into the applicator body, the trigger assembly 20 is engaged by the operator by pulling the grips together using a "squeezing" motion. The actuation of the spring loaded hook 21 about the grip attachment means 22 against the notched region of the extrusion rod 42 forces the bone wax into the bayonet 15 and out the tip 16. Within the bayonet, the wax is heated. Heating is achieved along a portion of the bayonet by the heating assembly.

The heating assembly comprises a heating element 31, which is operably connected to the current source (here, a battery 51). In one embodiment the heating element is a PTC element comprising conducting ink printed on filament paper. Other heating elements may be used and include thermofoils, wires and the like.

The connection between the heating element and the source of current may comprise any electrically conducting material. In one embodiment the heating element connector 32 comprises electrically conducting lines of ink printed on filament paper. Connection between the heating element and the current source may be made via any type of connector such as a wire, conduit or metal strip, filament or string. Shown in the figure is a battery connector 52 operably connecting the battery 51 to the heating element 31 via a heating element connector 32. The battery connector 52 is operably linked to the battery via a battery connector means 53 (shown in FIG. 5). An opening in battery housing 19 is used for receiving the battery connector. It is not necessary that the heating assembly cover the entire length of the bayonet.

In one embodiment, the heating assembly covers at least 40 percent of the bayonet. The heating assembly may be designed to cover from between 30-60 percent, between 20-80 percent or between 10-95 percent of the length of the bayonet.

For optimal wax heating, it is important to control the temperature along the bayonet. Insulating means 33 may be used to achieve this objective. Insulation around or along the bayonet may comprise a solid molded material applied to the surface of the heating mechanism or element or may be wrapped around the outside. Insulation may comprise a single layer or multiple layers. In one embodiment, the insulation 33 is comprised of plastic, plastic film or sheet, MYLAR™.

In a further embodiment, the insulation may be covered with one or more layers of heat shrink tubing 34. This tubing may be made of fluorinated ethylene propylene (FEP) heat shrink tubing or other suitable material.

Figure 4:
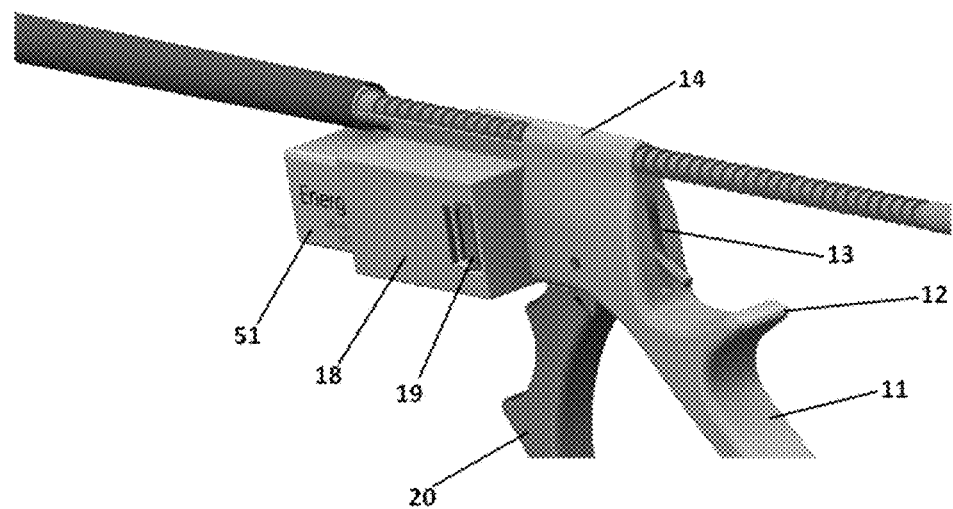
FIG. 4 illustrates further details of the applicator body.

FIG. 4 shows further details of the applicator body. Above the rear grip 11, is a rear grip guard 12. This guard serves to stabilize the device in the hand of the operator. The rear grip also contains a passage 13 through which extends a lever for disengaging the spring loaded hook and consequently the wax extrusion rod from the device.

Atop the applicator body is a mounting platform 14. This platform may be used to attach (either temporarily or permanently) an alignment device, sight, camera, mirror, fiber optics, laser, scope or other optical tool to aid in the alignment or positioning of the bone wax applicator. The platform may also serve as an attachment point for a surgical instrument, light, handle, clip or any device that may be useful in connection with the utilization of the bone wax applicator.

Figure 5:
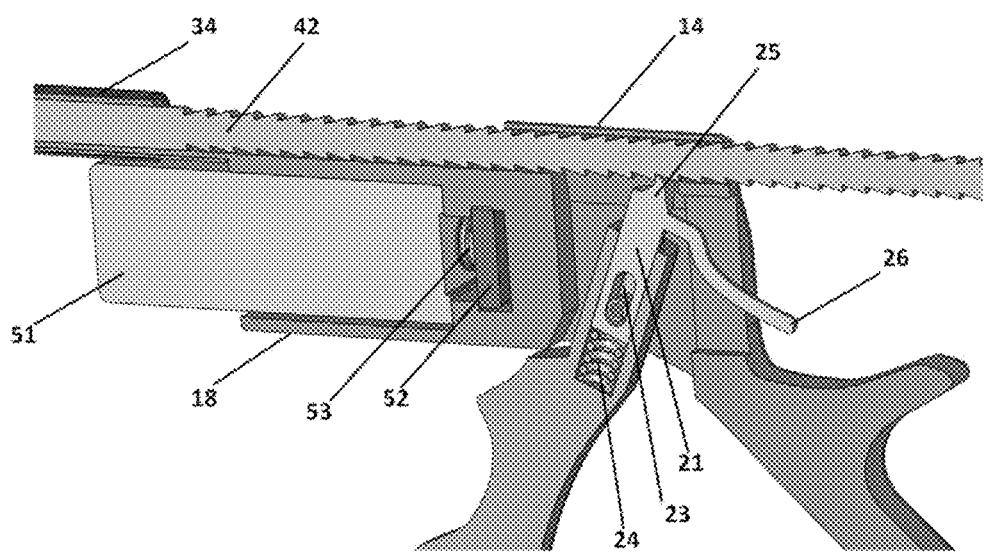
FIG. 5 illustrates the front grip trigger assembly.

The actuation of the notched region 42 of the wax extrusion rod through the wax loading chamber and into the cavity of the bayonet is illustrated in FIG. 5. Here, a spring loaded hook 21 centrally positioned in the shaft of the front grip and supported by a spring 24 engages the notched region in a ratchet type mechanism forcing the wax extrusion rod forward.

A groove 23 in the spring loaded hook allows the spring loaded hook to slide along the longitudinal axis of the front grip about the attachment means. In operation, the hook member 25 of the spring loaded hook is forced against the notched region 42 and may be disengaged by the operator pressing and holding down the lever 26.

Figure 6:
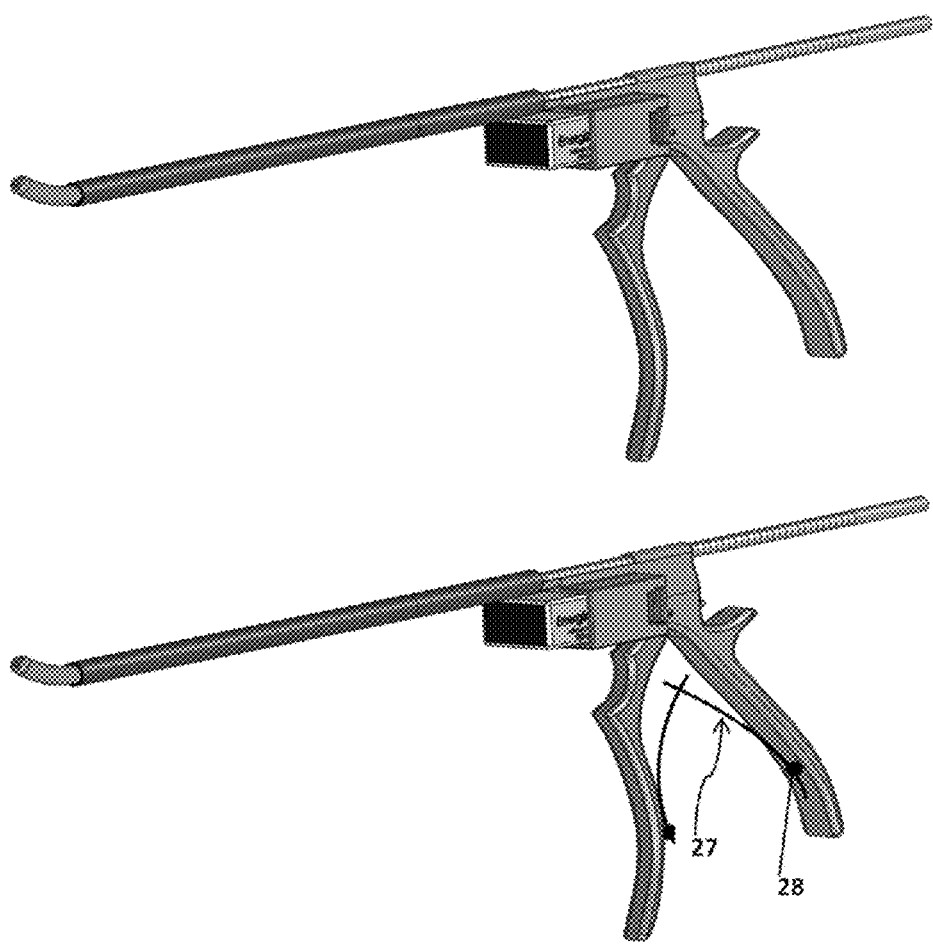
FIG. 6 illustrates alternate embodiments of the bone wax applicator, with and without tension means.

The bone wax applicator may be fitted with tension means 27 attached to the grips or trigger mechanism by any tension attachment means 28 including, but not limited to screws, pins, hooks and the like. Alternate embodiments of the bone wax applicator, with and without tension means, are shown in FIG. 6.

Figure 7:
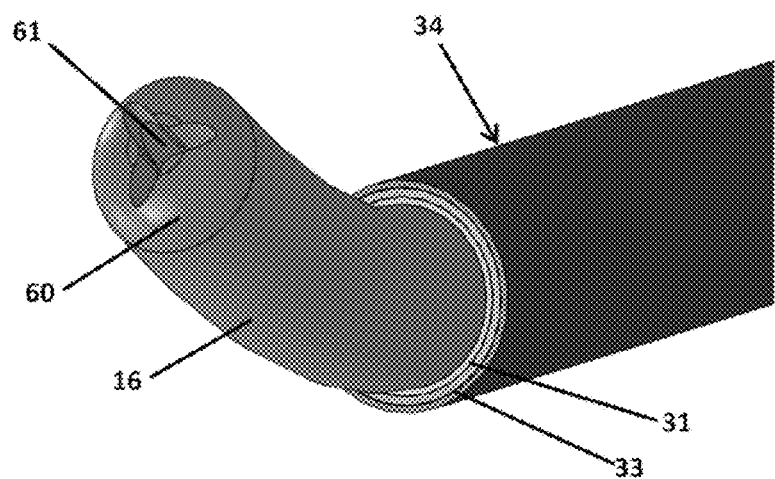
FIG. 7 illustrates one tip design of the present invention.

FIG. 7 illustrates one tip design of the present invention. As shown in the figure, the tip 16 may be configured or manufactured to be contiguous with the bayonet. The tip may represent at least 2, at least 3, at least 5, at least 10, at least 25, at least 30, at least 40 or at least 50 percent of the length of the bayonet.

Tips may be made as variable attachments to the bayonet.

Tips may be straight or have an angle of incline from the horizontal as measured along the longitudinal axis of the bayonet. The tip shown in FIG. 7 is a contiguous angled tip.

The tip surface 60 shown in FIG. 7 is rounded and smooth. In alternate embodiments the tip surface may be of any shape including square, triangle, or any polygonal shape with any number of sides or facets. According to the present invention, the tip cavity 61, may have an internal diameter equal to or smaller than the bayonet. The cavity may terminate in one or more holes or ports and may be of any shape, bevel or size relative to other ports or the bayonet internal diameter. Shown in FIG. 7 is a single port tip with a clover leaf cavity having internally beveled edges.

Figure 8:
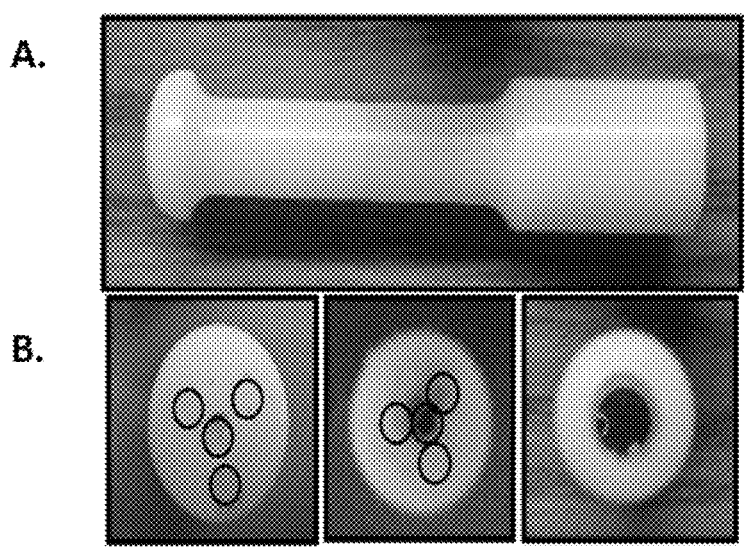
FIG. 8 illustrates alternate cavity embodiments for a smooth rounded surface tip.

FIG. 8 illustrates alternate cavity embodiments for a smooth rounded surface tip. FIG. 8A shows a side view of a straight tip attachment with a rounded smooth surface. FIG. 8B shows the end view of three cavity configurations, two multi-cavity and one single cavity design. It is shown that multi-cavity designs may include overlapping cavities or distinct cavities.

Figure 9:
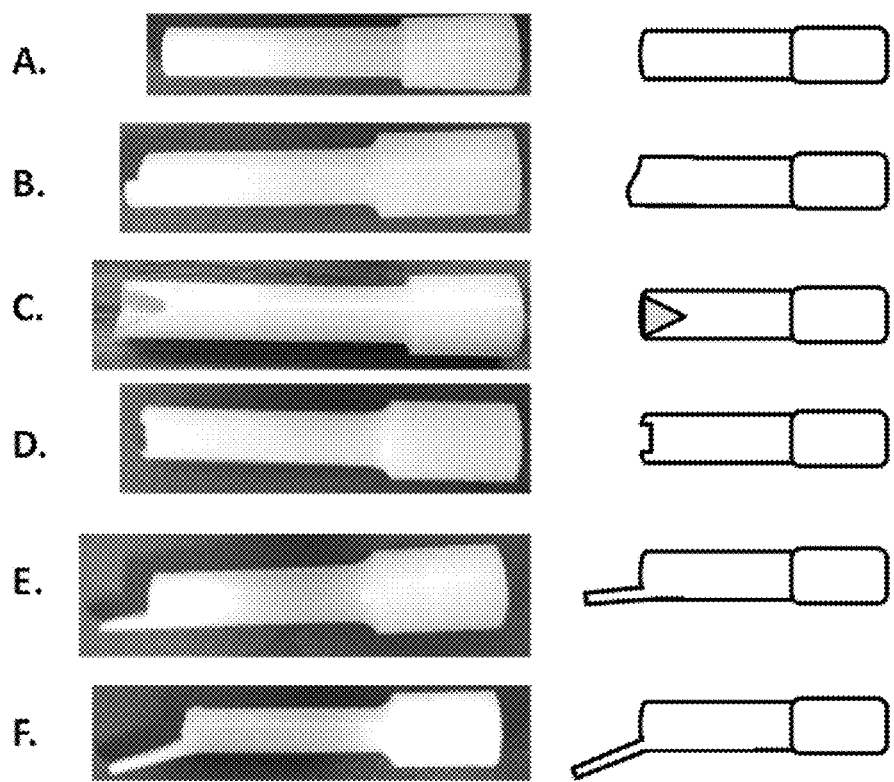
FIG. 9 illustrates six additional tip designs of the invention.

FIG. 9 illustrates six additional tip designs of the invention. FIG. 9A shows a straight tip with a rounded surface and smooth cavity exit. FIG. 9B shows a straight tip with a beveled cavity exit. FIG. 9C shows a straight tip with a triangular notched cavity exit. FIG. 9D shows a straight tip with a square notched cavity exit. FIG. 9E shows a straight tip with a straight lip (spatula) cavity exit. FIG. 9F shows a straight tip with an angled lip (spatula) cavity exit.

Figure 10:
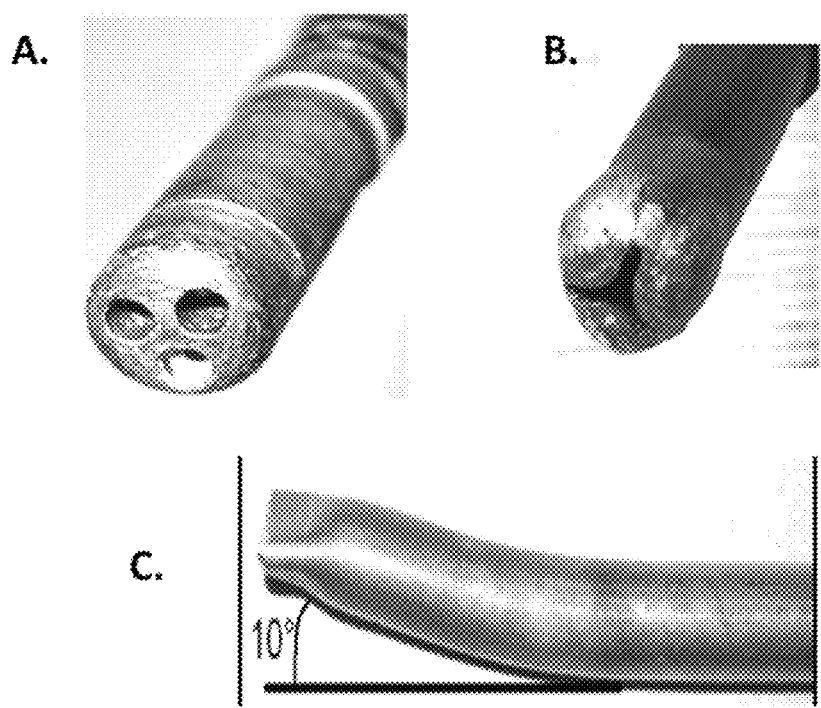
FIG. 10 shows images of photographs of three different tip designs which were manufactured.

FIG. 10 shows images of photographs of three different tip designs which were manufactured. FIG. 10A shows an angled tip with a smooth surface and three exit cavities. FIG. 10B shows a straight tip with a smooth surface and one clover leaf exit cavity. FIG. 10C shows an angled tip with a flattened exit cavity. The angle of the tip is 10 degrees. The angle of the tips of the invention can individually range from 5-90 degrees. In some instances, it may also be desired to have an angle of greater than 90 degrees, for example 90-120 degrees in order to apply bone wax to an obscured surface.

When manufactured as an attachment, tips may have rotating heads, multiple heads or be configured as a separate device with different heads, surfaces or cavity. The tips may be manufactured of material that differs from that of the bayonet and as such may be bendable or independently positionable. A multi-head or tip design would allow for the application of bone wax to more than one surface at a time.

Figure 11:
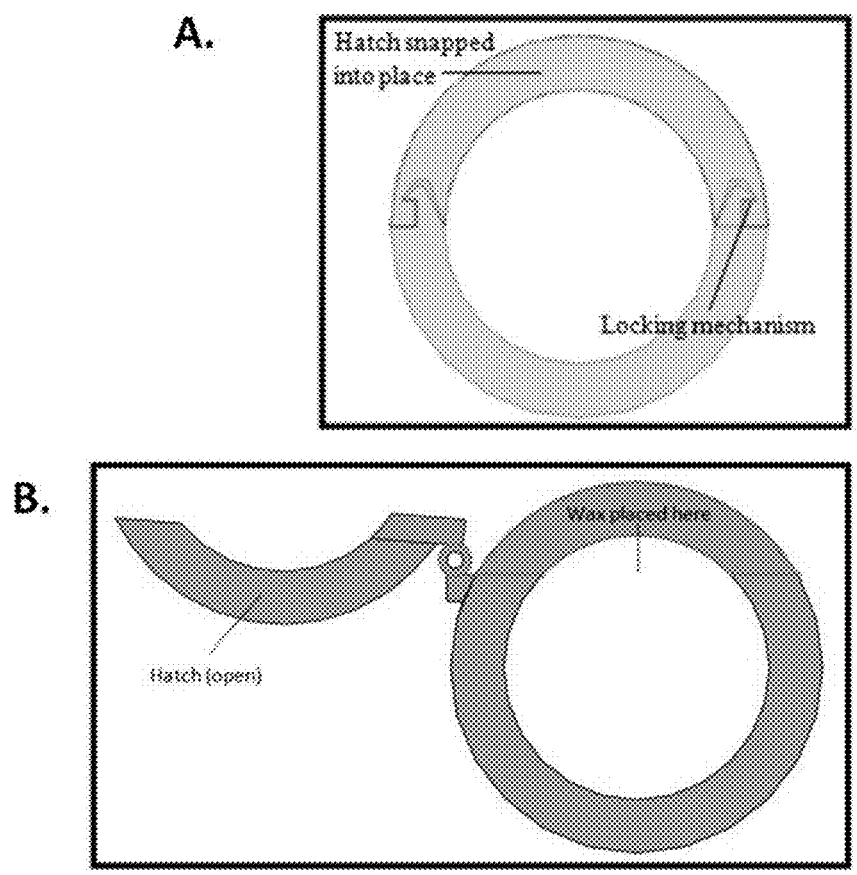
FIG. 11 illustrates the hatch chamber closing mechanism for the wax loading chamber.

FIG. 11 illustrates the hatch chamber closing mechanism for the wax loading chamber. In this embodiment, the wax loading chamber is configured with a hatch cover which can lock into place as shown. This configuration is advantageous in that it reduces the exposure of the wax to the surgical field or external environment.

Figure 12:
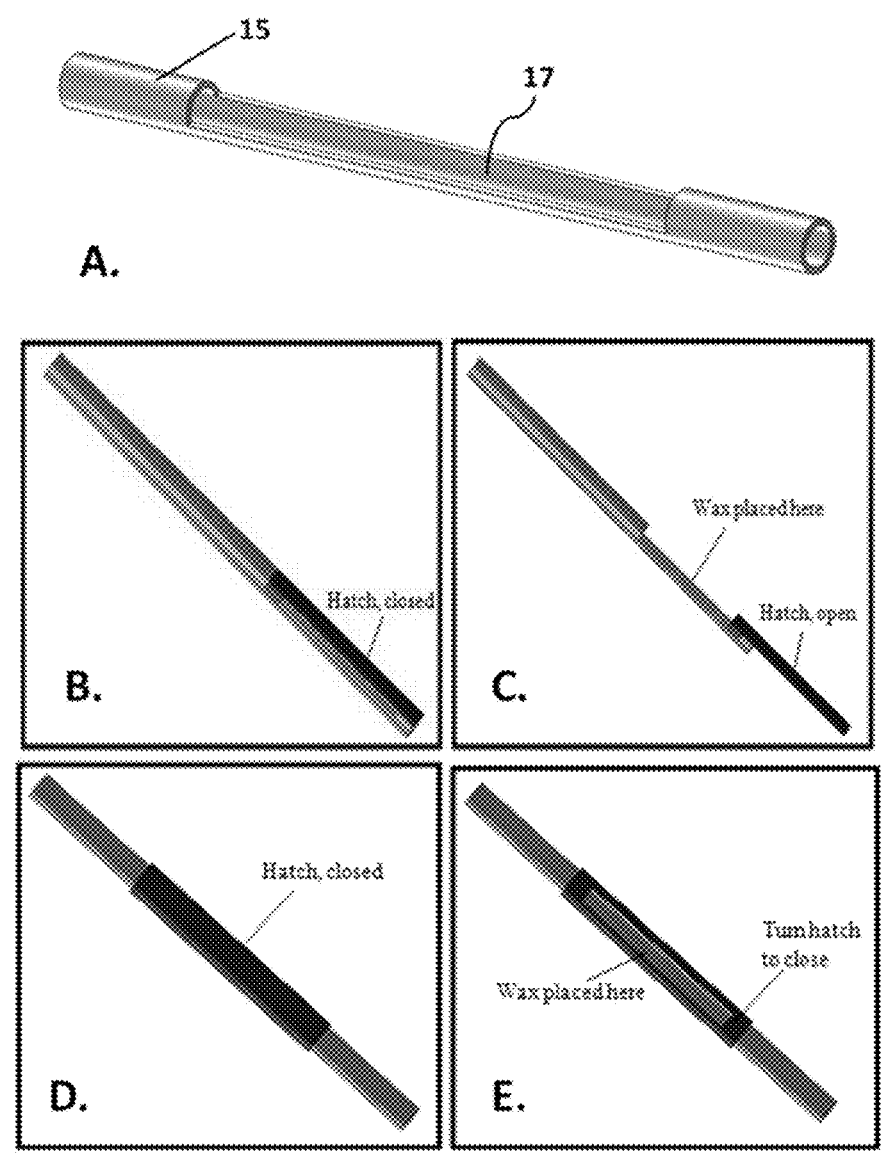
FIG. 12 illustrates alternative wax loading chamber enclosures.

Other wax loading chamber enclosures are shown in FIG. 12. Here, a sliding hatch and a rotating hatch are shown.

Figure 13:
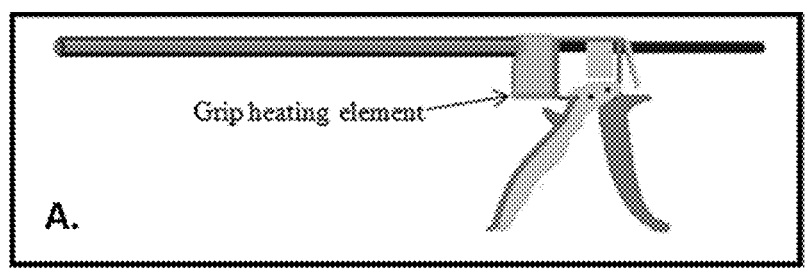
FIG. 13 illustrates alternate placement of the heating element of the invention.
Figure 13:
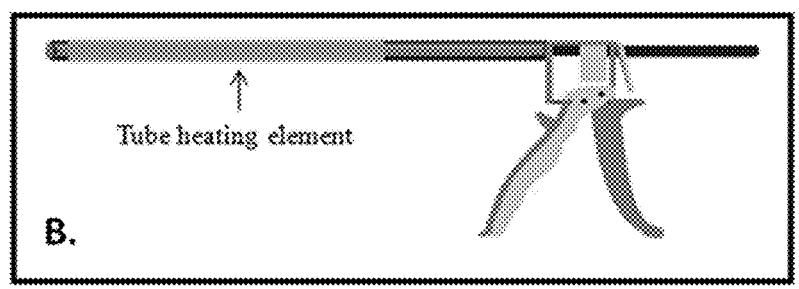

FIG. 13 illustrates alternate placement of the heating element of the invention. FIG. 13A illustrates a grip hearing element while FIG. 13B illustrates a tube (bayonet) heating element.

Figure 14:
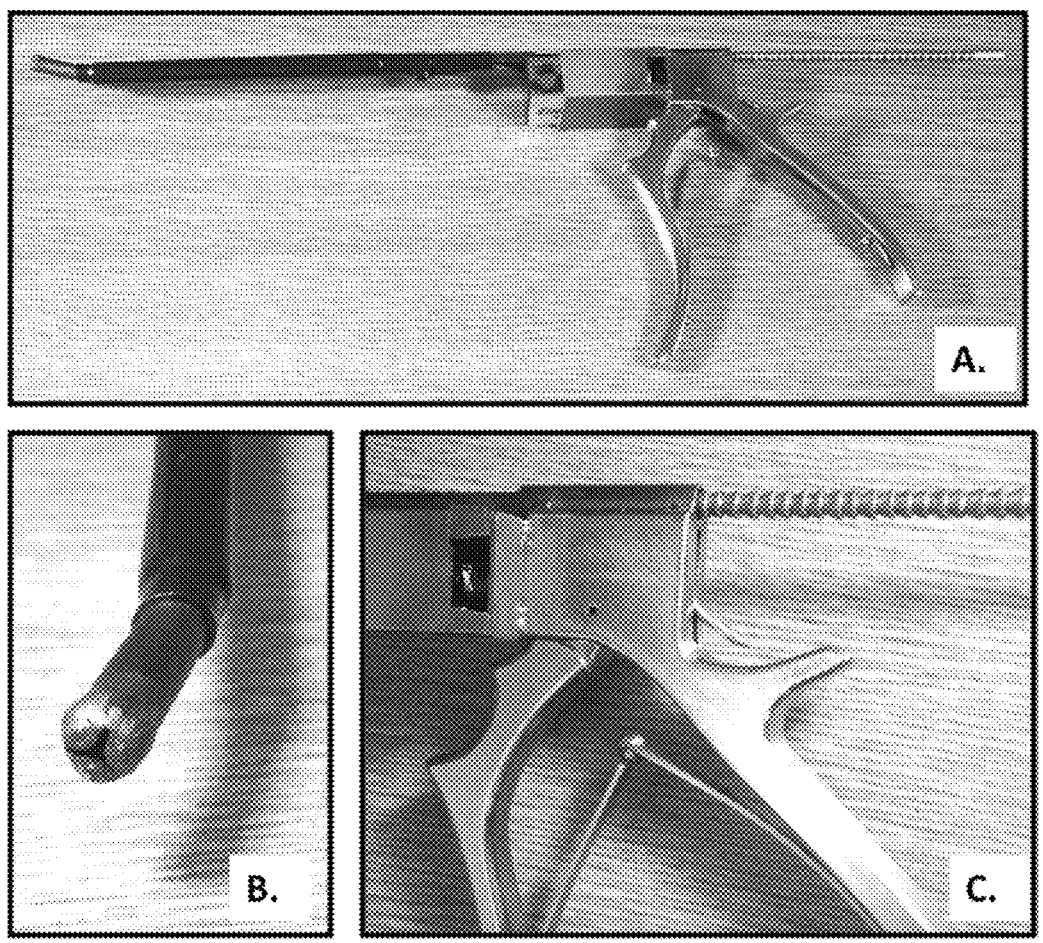
FIG. 14 shows images of photographs of a prototype of the present invention, showing the entire bone wax applicator, the tip and the applicator body and trigger means.

FIG. 14 shows images of photographs of a prototype of the present invention, showing the entire bone wax applicator (FIG. 14A), the tip (FIG. 14B) and the applicator body and trigger means (FIG. 14C).

Unless otherwise defined, all technical and scientific terms used herein have the same meaning as commonly understood by one of ordinary skill in the art to which this invention belongs. Although methods and materials similar or equivalent to those described herein can be used in the practice or testing of the bone wax applicator featured in the invention, suitable methods and materials are described below.

All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Applicator Design

Initial design efforts were directed to optimizing the application of the bone wax. To this end, three designs were tested. These included a retractable applicator, a modular applicator, and a roller applicator.

The retractable applicator investigated involved application of wax to the tip prior to application. In this embodiment, the tip is retracted into the outer shell and the applicator is inserted into the surgical site. The surgeon exposes the tip by pressing the outer button, and then applies the wax by depressing the inner button.

In the modular applicator, the grip and the tip designs are separated. Bone wax is added to the device by manually placing a small amount inside the tip before connecting it to the grip. Multiple tip designs such as those of FIG. 8 could be used.

While only three tip designs are shown, this modular design could allow for numerous other tip design alternatives. In particular, one tip design alternative could allow for bone wax to exit through a side port, and another could apply wax through a vertical port. While the modularity of the tips is an advantage of this design, attaching the proper tip may prove cumbersome and aggravating in the operating room environment.

The roller applicator design alternative uses a syringe to push wax onto a roller. As the handle is compressed, the flexible bar attaches to notches in the syringe and pushes bone wax down the device shaft. When the handle is released, the metal bar releases from the syringe and returns to the resting position. The surgeon then could use the roller to apply an even layer of bone wax to a desired bone surface.

Although novel in design, the roller applicator has many design flaws. The roller tip requires lateral movement that the small incision does not afford. Furthermore, the adhesive properties of the bone wax may cause rotation problems with the roller. Due to these limitations, this design alternative was abandoned.

A common theme among the preliminary design alternatives was the syringe-like mechanism. One concern was that unheated wax would be too stiff to squeeze out of a syringe outlet with an outer diameter of 8 mm or less. To investigate this concern, tests were performed using bone wax and two syringes, each with a 4.5 mm diameter outlet. The two syringes had an inner diameter of 15.6 mm and 14.4 mm, respectively. The bone wax was handled as minimally as possible with gloved hands to refrain from heating the bone wax via body warmth. The bone wax was placed in each syringe and the relative difficulty of squeezing out the bone wax was assessed.

Test results revealed that wax was more easily expelled from the 14.4 mm syringe. It was hypothesized that this was due to the smaller difference between the syringe diameter and outlet diameter. The room temperature bone wax proved to be difficult to squeeze out of the syringe with one hand. The tests were repeated after the bone wax was warmed with a gloved hand, which greatly increased the ease with which the bone wax could be squeezed out of the syringes.

The tests strongly suggested that the syringe design alternatives should provide a method of giving users a mechanical advantage in expelling the bone wax. The results also suggested that the bone wax applicator should retain a similarly sized outlet as the inner diameter to ease wax extrusion.

A proof of concept test was then performed to determine if a mechanical advantage could be sufficient to extrude unheated wax. A lever arm was used to push a syringe plunger through a straight tube approximately eight inches in length.

As the syringe tube inner diameter and the outlet diameter were the same size, the wax was easily extruded from the tube. Although the proof of concept prototype was unable to conclusively demonstrate the feasibility of using a mechanical advantage for unheated wax extrusion, there were two important results. Firstly, it was found to be nearly impossible to control the wax extrusion when the outlet was the same diameter as the tube, for there was nothing to prevent the wax from falling out of the device. The team therefore considered adding a slight taper to the tip, although not so much as to greatly increase the force required for wax extrusion. Secondly, the testing revealed that it took a long time to prepare and reshape the bone wax so that it could be loaded into the end of the tube. As the final bone wax applicator needed to improve the ease of applying bone wax, it was decided to consider methods of adding wax into the device. Such wax loading designs are described in Example 4.

As the previous test was inadequate in determining if a mechanical advantage would be sufficient in extruding bone wax, a more rigorous test bench was created. The acrylic test bench consisted of a set of square plastic channels, which varied the inlet and outlet sizes, as well as the taper between the two cross-sections. The dimensions are given in Table 1.

TABLE 1

Test bench channel dimensions

| Inlet diameter (mm) | Taper length (mm) | Outlet diameter (mm) |
|---|---|---|
| 6 | 10 | 5 |
| 6 | 10 | 4 |
| 6 | 5 | 5 |
| 6 | 5 | 4 |
| 6 | 2 | 5 |
| 6 | 2 | 4 |
| 5 | 10 | 4 |
| 5 | 10 | 3 |
| 5 | 5 | 4 |
| 5 | 5 | 3 |
| 5 | 2 | 4 |
| 5 | 2 | 3 |

The channels, which were precisely cut using a CNC machine, were cut square due to limitations in rapidly prototyping models that included rounded slopes. However, a circular channel was preferred in the final design to maintain a symmetrical design with no sharp edges. The test bench design required two symmetrical pieces to be clamped together during tests, and is a concession both to manufacturability and ease of cleaning.

Wax strips of approximately 4 cm in length were placed into the channels. A square piston that fit into the channel was used to push out the bone wax. For each test, a constant force was applied to the piston (48 N), and the time needed to extrude one centimeter of unheated bone wax was recorded. Six trials were performed on each of these channels.

The results from the quantitative force tests for the 6 mm inlet port channels suggested that wax flow rate is independent of taper length. However, flow rate did change with outlet diameter. Tests suggested that a smaller outlet diameter resulted in slower flow. While individual tests fluctuated more than desired, this latter conclusion was expected and further validated the overall testing. Thus, to attain a larger wax flow rate, the device was designed to have a larger outlet to inlet ratio, regardless of taper length.

In an effort to determine the necessary mechanical advantage, a blind test on eight individuals was performed to find the force that could be exerted comfortably. The test suggested that humans could exert an average grip clenching force of 15 N. The acrylic tube tests were conducted with a 48 N constant downward force. Thus, a design that implemented a 4:1 mechanical advantage was considered sufficient to extrude bone wax without use of a heating element. From these results, the retractable applicator design was abandoned.

After determining the necessary mechanical advantage for the device, subsequent design efforts focused on four sub-components: grip designs, tip designs, wax loading designs, and heating element designs. Each are discussed in the following examples.

Example 2

Grip Design

Five grip design alternatives or trigger assemblies were evaluated and tested.

1. Lever Arm. The lever arm is the simplest grip design. The top lever pushes a plunger through the tube attached to the bottom lever, extruding the wax. The tube travels along a track cut into the bottom lever so that it remains concentric with the plunger and torque is not experienced as the plunger is pushed down.

A three-dimensional printed model of the lever arm was developed. This proof-of-concept was ergonomically awkward and was very difficult to control the tube from which the bone wax was extruded. This suggests it would be less precise in applying bone wax to a specific location.

One advantage of this design is that it can be modified for the necessary mechanical advantage, which is based on the ratio between the lever length and the distance from the plunger to the hinge. The mechanical advantage translates a large force to a small distance. Furthermore, the plunger can only move a set distance; meaning only small amounts of bone wax can be extruded before reloading is necessary. Due to these reasons this design was abandoned.

2. Worm Gear. The worm gear design works by rotating a side-mounted lever. Angled gears cause the central worm gear to rotate in sync with the lever arm. The rotation of the worm gear pushes the cylindrical plunger downward, forcing the wax out to the tip.

To assess the user interface of the design, a three-dimensional model was printed. Although the model did not have the inner gears, it provided insight into other aspects of the design. Firstly, the design cannot be used with one hand because it requires one hand to stabilize the device while the other hand rotates the hand crank. Secondly, in order to get a sufficient mechanical advantage, the angled gears must be several centimeters in diameter, which blocks the surgeon's view. The internal mechanism also has numerous moving parts that make it more susceptible to jamming and manufacturing defects than simpler designs, thereby making it less reliable. Due to these disadvantages, the team abandoned this design.

3. Ratchet Gear. This design uses a ratcheting mechanism to extrude bone wax. A bending stop-pin next to the circular gear allows the gear to rotate in one direction, but prevents the gear from rotating backwards. The user squeezes the handle, which rotates the gear with a push-pin located on the pivoting handle piece. The rotation of the gear moves the plunger downward to extrude the wax. A compression spring (not shown) between the two handle pieces forces the pivoting handle section to revert back to its starting position. By design, the push-pin bends slightly as the handle returns to its fully open position, allowing the lever handle to move while the gear remains stationary.

This design provides a mechanical advantage that depends on the size of the circular gear and where the force is applied on the handle. The current design only allows for a single use, as the stop-pin prevents the plunger from being pulled back to its original position; however, modifications are possible. A three-dimensional printed model of the design was created. The initial printing suggested that push-pin and the stop-pin were too small and weak to adequately turn or stop the gear rotation, and might cause the device to be unreliable. However, the overall design was ergonomically similar to medical devices already used during surgeries, and preliminary testing demonstrated that it was both easy to use, and easy to precisely direct where the tip was pointing.

4. Caulking Gun. Instead of a gear, the caulking gun design uses a friction-spring mechanism to grip the plunger and slide it down the tube. A proof-of-concept model was constructed using the grip of an actual caulking gun with an aluminum tube attached. One advantage of the design is that the plunger is retractable, and therefore allows for the device to be refilled.

The mechanical advantage of this design is the ratio of the length of the bottom handle to the distance between the two screws on the lower handle. While the proof-of-concept was large and bulky, subsequent iterations of this design were streamlined and lighter to improve visibility for the surgeon. The caulking gun design was more robust and reliable than the other grip designs, and was also easy to use.

5. Spring Loaded Hook. The spring-loaded hook design was created in response to faults in the caulking design. See FIG. 5. It works in conjunction with a notched rod to extrude bone wax. The design uses a spring loaded hook having a hook member that slides in and out of the trigger assembly. A spring in compression between these two pieces ensures contact between the hook member and the notched extrusion rod. When the handle is released, a spring between the two handle pieces forces the handle pieces apart. The shape of the hook member, along with the notch design, allows for the spring loaded hook to compress the spring slightly, allowing it to glide over the rod without pulling it backwards. There are significant advantages to this design. Firstly, there are few parts compared to prior examples. Secondly, most of the design is internal. Thirdly, it is relatively easy to incorporate a release mechanism into the design. By pushing down on the lever, the connection between the rod and the hook member of the spring loaded hook is disengaged, which allows for the extrusion rod to be retracted. Due to the force on the lever, the selected material is required to be very strong, such as stainless steel.

Example 3

Tip Design

The tip is the outlet of the bone wax applicator that shapes and spreads the wax. It plays a key role in controlling the wax application. Numerous tip designs were evaluated throughout the design process. They were divided into four categories: regular tip, modified tube tip, spatula tip, and mushroom tip.

1. Regular Tip. The regular tip is the simplest tip in design. It is essentially an extension of the tube, but with a slightly smaller diameter. The smaller diameter is meant to compress and shape the wax prior to application. Although the simplicity of this design is appealing, it does not provide a large surface to spread the wax onto the bone. One example is given in FIG. 9A.

2. Modified Tube Tip. Three modified tube tip alternatives were investigated, all of which are altered regular tips. The one-notched tip, FIG. 9C, consists of a regular tip with a small lip that can be used to spread the wax. Similarly, the two-notched tip, FIG. 9D, has two lips that can shape the wax. The slanted tip, FIG. 9B, is composed of a regular tip with an angled cut. All of these modifications were meant to facilitate in shaping and spreading the wax. However, a disadvantage of these designs is that they are unfamiliar to the user, and they are unidirectional, meaning the device requires appropriate orientation in order to spread the wax.

3. Spatula Tip. The spatula tip design is similar to the tip of a Penfield applicator. The user extrudes the wax from the tube onto the tip, and can use the slanted surface of the tip to scrape or press the wax onto the bone. This design would be used similarly to the current procedures, and would be familiar to new users. The primary disadvantage is that the tip design is unidirectional and requires appropriate orientation to apply the wax in the desired direction, thus it is more difficult to use than other tip designs. It does, however, allow bone wax to be applied to multiple surface angles, as the spatula would facilitate application to side surfaces. Spatula tips of the present invention are shown in FIGS. 9E and 9F.

4. Mushroom Tip. The mushroom tip design consists of a symmetrical convex plate with an exit port for the wax at the center. See FIG. 8. Although the tube has an outer diameter of 7 mm, the convex plate is 10 mm in diameter. The extra area on the tip maintains a large outlet port and provides a larger surface to apply the bone wax. The mushroom design can have varying numbers of exit ports or openings. See FIG. 8B. Several possible configurations of exit ports were designed— only one exit port, four discrete exit ports, and four exit ports conjoined together (like a clover). Having multiple exit ports that are smaller in size is more desirable, so that the wax is extruded across a larger surface area of the tip and can be applied more easily. Unlike the spatula tip, this tip is not unidirectional, so the wax may be applied in any direction.

Example 4

Wax Loading Design

The method of loading the bone wax into the device is a crucial component of the overall design. It is possible that the final manufactured device will be preloaded with wax. However, a method for adding bone wax to a stand-alone applicator would be desired for maximum flexibility. A design that does not allow bone wax to be added easily will be bothersome and aggravating, and may discourage surgeons from using the device. Six wax loading design alternatives were evaluated.

1. Bone Wax Press. The bone wax press design presses a packet of wax into the extrusion tube of the device. The bone wax press design is limited in width by the size of the tube's inner diameter; however, the length can be as long as desired. Since the thickness of the bone wax is initially 5 mm thick, the design interfaces with the initial bone wax sample, so long as the length of the press opening is greater than the bone wax sample length. As the press significantly protrudes from the side, it cannot be located on the part of the device that enters the incision. While the current protruding design limits visibility for users, it could be relocated on a different side to increase visibility.

2. Open Hatch. A more basic loading system would have an open hatch in the tube creating a chamber in which the wax may be inserted. The hatch would be located near the top. The wax would be cut to a size that fits the diameter of the tube. After the wax is inserted into the hatch, the extrusion rod would be used to push the wax toward the tip so that more wax may be added. See FIG. 12A.

3. Snap-On Hatch. A second wax loading system uses a snap-on hatch on the side of the bayonet or tube. The wax is rolled (or otherwise shaped into an appropriate size) and placed into the opening. The hatch is then snapped into place to close the gap. The snapping mechanism is entirely contained within the walls of the tube to prevent disturbing the flow of the wax inside the tube, and to refrain from blocking the surgeon's view with protruding parts. In addition, the snapping mechanism is designed to prevent removal of the hatch after it has been locked in place. This ensures that the hatch will not fall off during wax extrusion, and enforces the disposability of the device. The materials for the design must be carefully selected, as the hooks are required to bend slightly, but not break off. See FIG. 11A.

4. Hinged Hatch. The hinged hatch design allows users to place a rolled piece of wax into an opening on the side of the tube. This design employs a hinge to keep the hatch attached to the body of the device to prevent the cover from being dropped or lost. Despite the small size of the hinge, its protrusion beyond the tube may limit the surgeon's field of vision. In addition, the actual size of the hinge may be too difficult to manufacture. See FIG. 11B.

5. Sliding Hatch. In the sliding hatch design, part of the tube slides downward and exposes the inner tube for wax loading. It has no protruding parts and all of the parts stay connected. A disadvantage of this mechanism is that the wax may extrude into the crevices between the two parts of the tube if not designed properly. See FIGS. 12B and 12C.

6. Rotating Hatch. The rotating hatch functions similarly to the sliding hatch, except that it has an outer casing that rotates to expose the inner part of the tube. A disadvantage of this design is that it requires a larger diameter for the outer casing. The hatch could be placed toward the top of the grip, but then the wax would need to be pushed down a longer distance to reach the tip of the tube for application. Alternatively, the rotating hatch could be placed internally rather than externally, which would be similar to other medical equipment used. See FIGS. 12D and 12E.

Conclusion. The open hatch was deemed most desirable for initial prototype purposes as it does not require any moving parts, does not add any width to the overall device, and is simple and intuitive. An alternative is the rotating hatch, but since the wax significantly protrudes from the device, it makes the device bulky and impedes the visibility of the surgeon. The snap-on hatch, which does not allow for wax to be reloaded, would be acceptable as long as a significant amount of bone wax could be added in the initial loading process. The hinged hatch requires very small parts and the protruding hinge may impede surgeon visibility. While the current prototype uses the open hatch, future research and testing on the wax loading mechanism is recommended. Should the design be disposable, the optimal device would be preloaded with bone wax.

Example 5

Heating Element Design

Although a heating element was not necessary for a functional prototype, initial prototype testing demonstrated that the properties of heated wax were preferable to unheated wax. Heated wax spreads more easily and was much easier to apply during testing. The following sections detail the design process for the heating element.

1. Wax Temperature Testing. Testing was done to determine the ideal temperature range to heat the wax. Bone wax was set in a small beaker. The beaker was placed in a water bath. Using a hot plate, the wax was heated and the properties of the wax were observed as it heated up.

The qualitative properties of the wax were felt by hand as the wax heated up. Table 2 details the quality of the wax at varying temperatures.

TABLE 2

Temperature v. Quality

| Wax Temperature (° C.) | Quality |
|---|---|
| <30 | Hard |
| 30-35 | Starts to soften |
| 35-40 | Easy to spread with fingers |
| 40-50 | Very easy to spread with fingers |
| >50 | Begins to melt |

From this testing, it was decided to heat the wax to 45° C., as that was the median in the temperature range for wax of very good consistency. However, the introduction of a heating element presented new constraints. The outer temperature of the tube would ideally remain as close to 37° C. (body temperature) as possible, so as not to harm the patient or the doctors and surgical technicians handling the device. Thus, insulation must also be considered. The heating element should last at least one hour, which is approximately the length of time the doctor may need to use the applicator in a given surgical procedure. The device should be powered through a battery so as not to clutter the operating area with a power cord. Lastly, the device should warm the wax quickly.

2. Heat Source Locations. Another design consideration for the heating element was where the element should be located on the device. Two possible locations for the heating element were explored—at the trigger assembly (grip) or around the bayonet.

A heating element at the grip would rely on the conductivity of the material of the tube to transfer the heat to the wax inside. Containing the heating element within the grip does not influence how wax can be loaded into the device, and it maintains most of the dimensions of the device, thus requiring minimal adjustments to implement. However, having the element at the grip means that the element will have to reach higher temperatures in order to warm the wax, and insulating the heating element at hotter temperatures would be a larger challenge.

Alternatively, a heating element around the bayonet is advantageous in that it does not have to reach a temperature much higher than 45° C. However, such a heating element in addition to insulation adds material to the bayonet, and thus to maintain an outer diameter of approximately 8 mm, the inner diameter will have to be smaller, decreasing the amount of wax that can be stored in the bayonet. To retain the small diameter of the bayonet, the heating element needs to be very thin and flexible so that it can wrap around the tube.

Example 6

Heating Element Location, Size, Material and Insulation

Rather than immediately ordering and testing many different heating elements at various locations and sizes, a finite element model analysis was performed using COMSOL. This tool allowed estimation of the heating behavior of different heating elements before further pursuing a specific design implementation.

Four categories of the design were selected for further testing after the modeling: location of the heating element, size of the heating element, material for the tube, and insulation. All of the COMSOL models assumed a heating surface of 45° C., 15 cm of bone wax loaded from the tip end, and a 6 mm ID and 7 mm OD tube. The models were analyzed parametrically in time up until 30 minutes. 2D Axial Symmetry was assumed and the standard Heat Transfer Module for COMSOL was used.

1. Location of the Heating Element. As previously mentioned, the heating element for the caulking gun design could be located in two places: near the trigger assembly (grip) or around the bayonet. The grip heating approach was designed such that only the circular base of the bayonet in direct contact with the grip (excluding the threads) was heated. Results showed that aluminum performed best. However, even after 30 minutes, the bone wax did not reach 45° C., which was the desired temperature for optimal malleability.

The heating element was then moved to the outside circumference of the bayonet. A 1 cm heating strip that wrapped around the bayonet was drawn around the midpoint of the wax in the bayonet. The outer boundary of the heating element assumed perfect insulation, meaning this modeling represented the best-case scenario for the heating element. Results for heating around the bayonet showed that almost all of the wax reached 45° C. in the aluminum model. Thus, it was concluded that heating around the bayonet would be more effective.

2. Size of the Heating Element. Because the entire bayonet would contain wax, a larger heating strip could be employed to heat along the entire bayonet. To explore this option, a model was drawn such that the entire 15 cm of bayonet that contained the wax was encased in a strip of heating material. As with the 1 cm heating strip, this modeling assumed perfect insulation. Results showed that a heat strip that covered the entirety of the bayonet would be ideal.

3. Bayonet Material. The previous models used various materials for the bayonet: acrylic, DELRIN™, stainless steel, and aluminum. It was concluded that acrylic and DELRIN™ should not be used, as they act as insulators and resist heat transfer. However, the stainless steel and aluminum models facilitated heat transfer.

4. Insulation. To prevent the higher temperature of the bayonet and heating element from coming directly into contact with the patient's tissues, a layer of insulation was needed. Three materials were investigated for their low thermal conductivity polyimide (e.g., KAPTON™), MYLAR™, and STYROFOAM™.

A 1 mm thick layer of insulation was drawn around the entire bayonet, which encased the bayonet and the 15 cm heating strip around the bayonet. All three insulators had very similar results and none could decrease the outside temperature to the body temperature of 37° C. However, as thinner STYROFOAM™ would be difficult to handle, only KAPTON™ and MYLAR™ were explored further.

Example 7

Heating Methods

Having modeled the heating element with COMSOL, it was necessary to determine different methods of implementing the heating element. Details as well as advantages and disadvantages of each method are described herein.

1. External Heating Accessory. One heating method would be to use an external accessory heating device. When the bone wax applicator is not in use, it is placed on a stand or in a holster that warms the device and the wax. This heating element would require minimal alterations to the design of the applicator. However, the material used to construct the applicator is still an important consideration. While a viable option, an accessory device design was not further optimized.

2. Wire Element. An alternative way to heat the wax is to use a wire heating element. The wire may travel straight down the bayonet or it may coil around the bayonet circumference. It was hypothesized that a 9 V battery should be sufficient to power the wire and provide enough heat to keep the wax malleable without melting it. The material used to construct the applicator must be carefully considered, for if the applicator is not properly insulated the heat will be transferred to the environment or the patient rather than to the wax.

Figure 15:
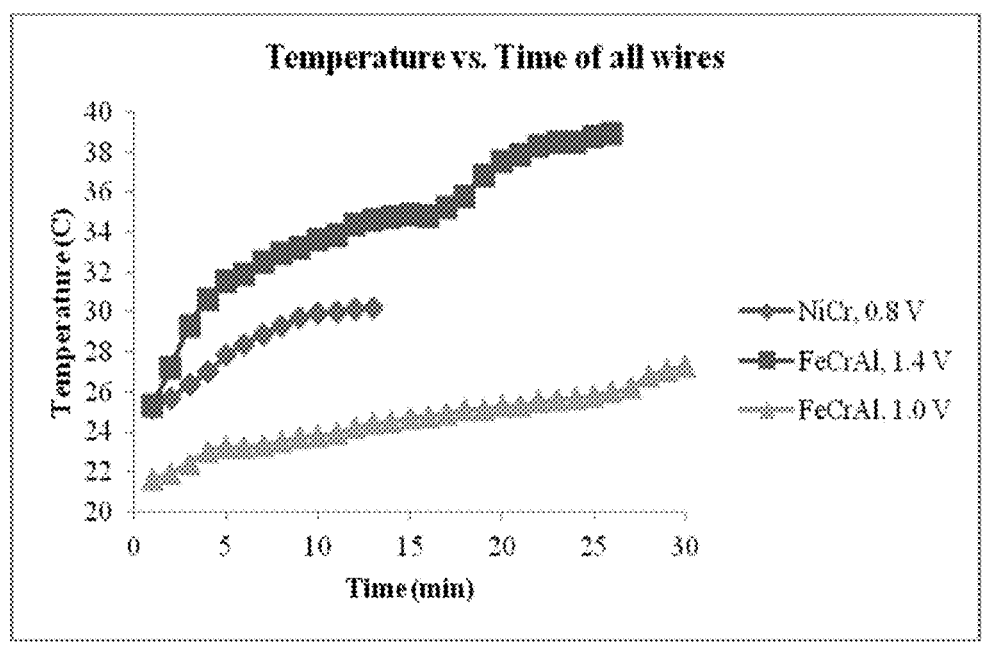
FIG. 15 shows the temperature profiles of various wire compositions used as heating elements.

Testing was done to assess the feasibility of using a wire to heat the wax. Two high resistance wires were evaluated: a NiCr alloy wire and a FeCrAl alloy wire. For the test, 2 ft of wire was cut and coiled around a steel bayonet that contained wax inside. The ends of the wire were connected to a power source. A thermocouple probe measured the temperature of the wax in the bayonet. The goal of the wire testing was to measure the temperature over time at different voltages. However, upon testing, it was discovered that the wires could only handle a limited amount of voltage. The temperature profiles are shown in FIG. 15. The most promising wire was the FeCrAl wire at 1.4 V. With that wire, the wax reached a temperature of 40° C. within 30 minutes. However, this heat up time was slow compared to that of the thermofoil and positive thermal coefficient (each discussed below).

3. Chemical Heating. Chemical compounds are another way to heat the bone wax. There are two primary methods to generate heat chemically. One is with a solution of powdered iron, sodium chloride, and charcoal, which heats up via air-activation. Another method is using sodium acetate, which requires a metallic trigger to initiate solidification and release heat.

To test the air-activated chemical solution, a commercially available heat pack was tested. The test sought to determine what temperature the chemical solution can reach, but did not test how long the heat lasts. The heatwrap was cut so that a thermocouple probe could be placed inside the solution and the temperature was measured.

Although the chemical powder did reach over 60° C. within 10 minutes, this design was not further pursued as other alternatives proved more promising.

The best scenario for implementing this method would be in a chemical sleeve, but heating accessories are not ideal in an operating room. Implementing within the device would be difficult because it would have to be enclosed in an airtight container, and then some mechanism for exposing it to air to activate the heat would be necessary. Enclosing the chemical within the device would be a major challenge in the manufacturing process. Also, it is unknown if chemical exposure to internal tissue is harmful.

Sodium acetate from a CVS/pharmacy Neck Heat Pack was also tested. 90 mL of solution from the heat pack was poured into a cup, and then a metallic trigger caused the solution to heat up. The sodium acetate also heats up quickly, and remains above 45° C. over the course of an hour.

Like the iron solution, the sodium acetate solution would also be difficult to implement. With a bayonet that is only 8 mm in diameter, adding a chemical layer is not practical. Additionally, when sodium acetate comes into contact with skin, it causes irritation. This could be a problem should the bayonet crack and this chemical solution enters the surgical wound of the patient. In general, the chemical heating methods are a possible alternative for the device but were initially deemed less promising than other alternatives.

4. Thermofoil. A method similar to a wire element is a thermofoil heating element. Thermofoils are resistive wires that have been flattened to increase the surface area of the wires. They are encased in thin, MYLAR™ sheets, and are very flexible, which allows them to be wrapped around the small diameter of the bayonet. The thermofoils vary in resistance and wattage output, which in turn varies the overall temperature. The thermofoil requires a temperature sensor and a control system to ensure that the temperature does not exceed the temperature constraint. This adds to the cost and complexity of the overall heating element.

Thermofoils, a control system, and thermistor and RTD sensors were purchased to evaluate this heating option. The thermofoils with higher wattage output per area density output the most heat, as expected. It was found that a wattage density of 5 W/in$^2$ was the minimum required output to ensure that the heating element could reach 45° C. at 9V. Higher wattage density heaters had faster heat up times.

As the thermofoil is not self regulated, it therefore requires a sensor and control system to set the temperature. Both the resistance temperature detector (RTD) sensor and the thermistor sensor are two options for temperature sensors. As the RTD sensor is 0.7 mm thick, has a fast reaction time to temperature changes, and is nearly linear with temperature in the 20-45° C. range, it was considered the optimal temperature sensor for this heating design. The implemented RTD sensor was the S651PDY24A RTD sensor created by Minco®.

Bang-bang (on-off), proportional, and PID (Proportional/Integral/Derivative) controllers were evaluated. Since it was not problematic if the temperature varied slightly (±1° C.), and since the bang-bang controller was the simplest design, this type of controller was chosen to control the thermofoil temperature. For preliminary tests, the CT-325 bang-bang controller, created by Minco® (Minneapolis, Minn.), was used. While this particular controller is about the size of a 9V battery, future work would seek to decrease the overall dimensions of the control system, should the thermofoil be implemented in the final device.

A third controller system, the CT-198 made by Minco® (Minneapolis, Minn.) works with select thermofoil heaters and does not require a temperature sensor. It instead determines the temperature by sensing a pulse of current into the thermofoil, and measures the varying resistance of the thermofoil, which changes with temperature. While this controller is optimal in that it does not require an additional temperature sensor component, it was not tested.

Testing was done on various thermofoils to determine what voltage was needed to power the thermofoils to reach the target temperature of 45° C. It was also considered to use thermofoils without a controller. However, as thermofoils are designed to be used with a controller, they would likely not be FDA approved without a control.

The first thermofoils tested were the KHLV105/2, KHLV105/5, and KHLV105/10, ordered from Omega, where 2, 5, and 10 indicate the wattage density per inch squared. The first test done on these thermofoils was meant to give an idea of how they behave. The foils were connected to a 9V battery and the temperature was measured with a thermocouple until they reached 45° C.

From this preliminary thermofoil testing, it was determined that 5 W/in$^2$ is the minimum wattage density required to generate enough heat with a 9V battery. Also, initial testing with the thermofoils demonstrated a much faster heat up time compared to that of a coiled wire. The 5 W/in$^2$ and 10 W/in$^2$ foils heated up to 45° C. within three minutes.

The 5 and 10 W/in$^2$ thermofoils were tested in more detail, in which temperature was characterized over an hour with different voltages. From these tests, the team concluded that the 5 W thermofoil requires a power source of 9V to reach the desired temperature, whereas the 10 W thermofoil requires between 5 and 7 V.

Additional thermofoils by Minco (Minneapolis, Minn.) were also tested. These additional thermofoils were not labeled by their wattage density, but rather by their resistance. Table 3 lists the different resistance for the thermofoils.

TABLE 3

Thermofoil properties

| Thermofoil | Resistance |
|---|---|
| HK5165 | 52.3 |
| HK5162 | 52.3 |
| HK5164 | 78.4 |
| HK5160 | 157 |
| HK5166 | 529 |

The Minco thermofoils were tested with a 9V power source and with a 9V battery. They were compared with the 5 W thermofoil. Testing suggested that lower resistance thermofoils reached higher temperatures. They also last over an hour with the 9V battery. Based on these tests, the 5 W thermofoil was optimal. However, since the thermofoil would likely require a controller, the team determined that a 10 W foil could be used, which would heat up faster than the 5 W thermofoil.

Testing was also done to ensure the functionality of the controller. The controller was tested with the 5 W thermofoil. It was set to maintain the temperature at 38° C. The test used a 9V battery as the power source. The controller was very successful at maintaining the temperature and did not significantly slow down the heat up time.

Figure 16:
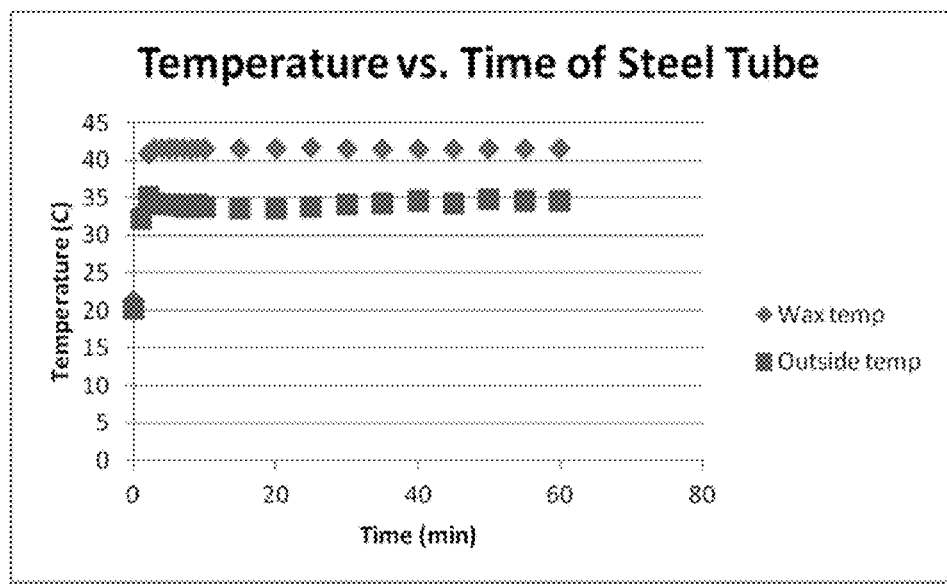
FIG. 16 shows the temperature of the wax and bayonet on heating.

Lastly, the 10 W thermofoil was tested with the controller and 9V battery. The controller was set to maintain a temperature of 41° C. The thermofoil was wrapped around a stainless steel bayonet with wax inside. Five layers of clear MYLAR™ were wrapped around the thermofoil and the outer temperature of the bayonet was measured. The test showed that the 10 W thermofoil would successfully heat the wax and maintain the heat over the course of an hour, and the MYLAR™ would sufficiently insulate the bayonet. The results are shown in the graph in FIG. 16.

Example 8

Insulation Testing for Thermofoils

Figure 17:
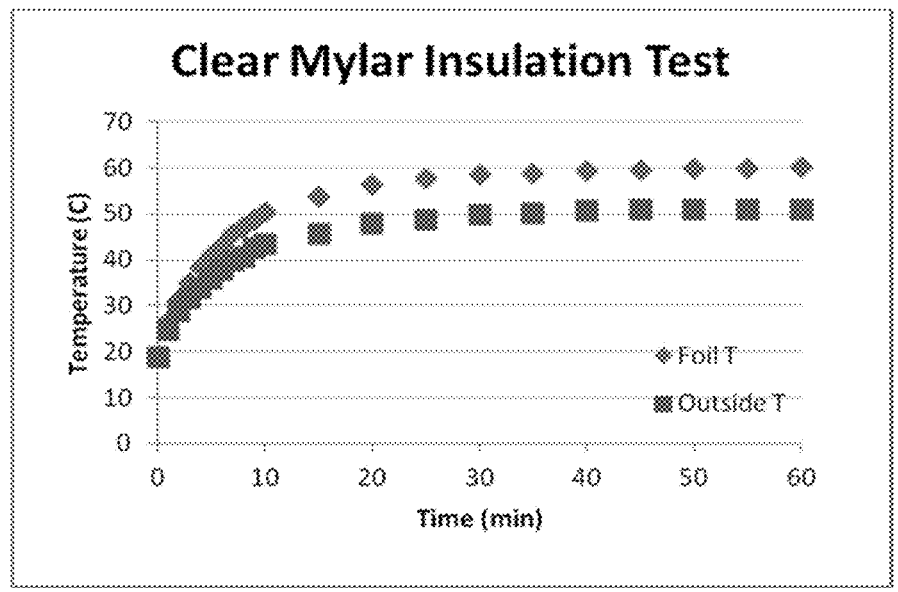
FIG. 17 shows graphs of the study of clear and reflective MYLAR as insulation to thermofoil heating elements.
Figure 17:
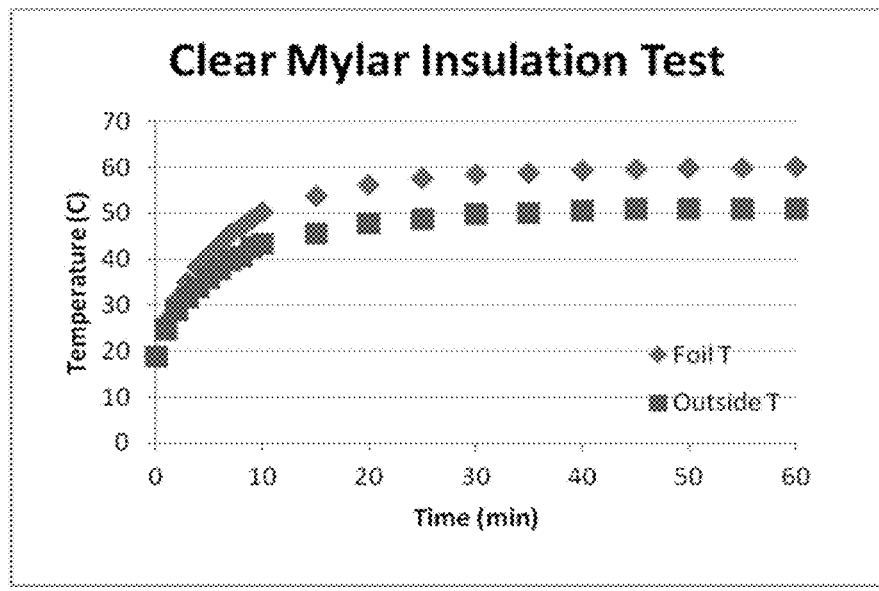

Two kinds of MYLAR™—clear and reflective were investigated. Five layers of MYLAR™ were wrapped around a 5 W thermofoil, which in turn was wrapped around the bayonet. The temperature of the thermofoil and MYLAR™ were measured. Both types of MYLAR™ kept the outer temperature approximately 7 degrees cooler than the thermofoil. The results are shown in the graphs of FIG. 17.

Example 9

Positive Thermal Coefficient (PTC) Heaters

Positive Temperature Coefficient (PTC) heaters have a nonlinear relationship between their resistance and temperature. As such, when the temperature increases, so does the resistance. This internal negative feedback ensures that the temperature of the strip will never exceed a fixed temperature for a given input voltage. This allows for a regulated final design without a feedback controller.

PTC elements exist in many forms; PTC thermistors resemble normal resistor, while PTC sheets are similar to thermofoils. PTC sheets can be screen printed, which allows for quick and inexpensive production of customized heaters. One concern about sheet printed PTC heating elements is that the printed wires may break if bent too sharply.

Both the PTC thermistors and the PTC sheets were tested. The PTC thermistors were considered as a possible method to heat the wax from the grip. However, modeling showed that heating at the grip is less feasible due to constrained methods of insulating the heating element. The thermistors were then considered as a possible controller, to be used in series with the thermofoil. The PTC sheets, which were obtained later, would be used similarly to the thermofoil, but without the need of a controller.

The team tested two PTC heating elements ordered from Murata (Smyrna, Ga.) at different resistances—one was a 470 ohm resistor, and another a 1.8 ohm resistor. Table 4 lists the equilibrium temperature observed at varying voltages for the resistors.

TABLE 4

Equilibrium Temperatures v. Voltage

| Resistor | Voltage | T (C.) |
|---|---|---|
| 1 × 470 ohm | 10 | 26.7 |
| 1 × 470 ohm | 15 | 30.6 |
| 1 × 470 ohm | 20 | 32.6 |
| 3 × 470 ohm in series | 10 | 23.9 |
| 3 × 470 ohm in series | 20 | 29.6 |
| 1 × 1.8 ohm | 1 | 31.7 |
| 1 × 1.8 ohm | 2 | 44.4 |

The 470 ohm resistor was tested individually and with three in series. The 1 Ohm resistor was tested individually. The 470 ohm resistor did not reach the target temperature of 45° C., either individually or in series with a voltage input of 20V, and thus would not function for the heating element requirements. The 1 Ohm resistor only requires 2V to reach 45° C.

As grip heating would be less practical than heating around the bayonet, the 1 Ohm PTC in series with a thermofoil was investigated. To test this, a 5 W thermofoil was placed in series with a 1 Ohm PTC and the temperature was measured after one hour. Based on the results, implementing a PTC in series with a thermofoil could regulate the temperature, but would require a higher voltage source, so this setup is less desirable.

In a wax transmission test, a 5 mm thick piece of wax (opened directly from the wax packet) was set above a 10 W thermofoil. The temperature of the thermofoil and the top of the wax were measured to observe how the heat transfers through the wax. The results indicate that the time for each to reach 40° C. was about 40 minutes. This testing suggested that the heat transfer through the wax must be considered, as it does take some time to warm all of the wax. However, the wax in the bayonet will have a diameter of about 5 mm, and as the thermofoil will be wrapped around the circumference of the bayonet, the heat transfer will take less time than it did in this test.

The PTC sheets were tested similarly to the thermofoils. For testing, the PTC sheet was wrapped around a stainless steel bayonet, and the temperature of the wax was measured at 6V, at which point the PTC exceed 45° C. The data revealed as steep temperature increase to 45° C. in about 10 minutes with temperature plateaus at slightly over 50° C. by 20 minutes.

The PTC sheet was also tested with a 9V battery to determine whether a capacitor would be required to delay the initial voltage input to the PTC, so as not to ruin the PTC. Testing showed that too much current draw at the beginning would not be an issue. The data showed a peak at 55° C. at 10 minutes and a slight decline to 40° C. by 60 minutes, followed by a precipitous drop to 20° C. However, the PTC did not last as long as desired with the battery, suggesting that battery selection would need to be considered.

Example 10

Battery Selection

A simple circuit includes the heating element and the battery. As current flows through the resistor, or heating element in the design, it heats up and delivers that heat to the bone wax in the bayonet.

The relationship between voltage (V), current (I), and resistance (R) in the circuit is governed by Ohm's Law, which states that V=IR. Thus, for a 10 Ohm thermofoil and a 9 volt power source, the current through the circuit is 900 milli-Amps. A battery's working capacity can be described by its number of amp-hours, which is how long the battery can output a certain current. For example, a 9 volt battery with a 450 milliAmp-hour (mAh) capacity that is connected to a 10 Ohm resistor will last 30 minutes, for an ideally constant voltage and resistance.

However, as a battery is used, the amount of charge between the positive and negative terminals decreases over time, leading to a decreased voltage. This decreased voltage will cause a decreased current through the resistor, which in the design, is critical for heat generation. Thus, the ideal battery for this design would have 1) a high enough voltage to provide heat, 2) a high capacity to deliver heat for an hour, 3) have a low voltage drop over the course of a suitable time period, and 4) be small enough to not impede the device's functionality.

Initial tests with a 9 volt alkaline battery, chosen due to their high voltage for a relatively small size, allowed the thermofoil and controller combination to reach a steady state temperature for over an hour. However, to reduce the number of components on the device, the PTC elements were used. Because these PTC elements start with a very low resistance, a high amount of current is drawn initially to heat the element, causing the batteries to quickly deplete (both Temp and Voltage drop by 55 minutes). Thus, different battery configurations and new batteries, especially lithium batteries, were investigated.

By placing multiple batteries together in certain configurations, the power source specifications could be increased. If two batteries are connected in series, where the positive terminal of one battery connects to the negative terminal of another, the total voltage will be the sum of the two batteries, while the capacity remains the same. If two batteries have both positive or both negative terminals connected, the batteries are connected in parallel, which keeps voltage the same, but doubles the capacity. Due to size constraints, however, these configurations could not be implemented well to achieve the same voltage and capacity as 9 volt alkaline batteries did.

Figure 18:
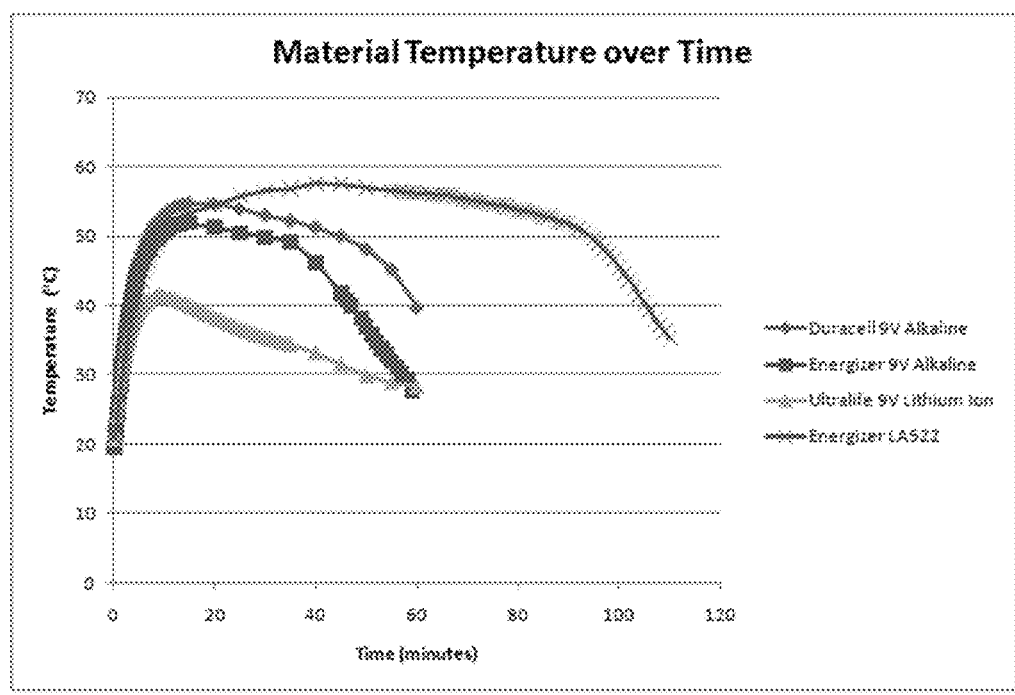
FIG. 18 shows PTC testing done with different batteries.

Lithium batteries were rated with much higher capacities than their alkaline counterparts, so theoretically, smaller batteries could be used to obtain the same voltage and battery lives. Preliminary tests indicated that these batteries, however, actually performed worse in temperature and battery lifetimes. The comparison is shown in FIG. 18.

The voltage of these batteries dropped to very low values once connected to the PTC load. Further analysis of the batteries noted that standard lithium batteries are not made for sustained high-current loads, such as the PTC elements used here.

The battery found to work well with the PTC is the Energizer LA522. Although it is a 9V lithium battery, it is designed for high current draw, and testing clearly demonstrated its functionality.

While the basic properties of bone wax have remained the same since its first use, unfortunately, so has our application of it. Bone wax handled directly from packaging, at room temperature, is not amenable to be used, rather it requires the surgical technician to mend it into a more pliable form. During testing, it was discovered that heating the wax increases its malleability such that for the first time bone wax can be applied with a greater degree of precision in microsurgical and minimally invasive approaches. Consequently, this translates to a quicker, easier, and safer application as less force is required from the surgeon to intercalate it into the trabecular bone. Furthermore, since the wax is more directly applied, less wax is used in shorter time—translating to time and cost saving.

Example 11

Advantages of the Present Invention

Detailed drawings of the prototype exemplar of the invention are featured and described herein. The bone wax applicator of the present invention fulfills two key aspects of bone wax application: 1) Using a heating element softens the wax to allow for more precise and effective application and 2) The applicator is specifically designed to be used in minimally invasive/microsurgical conditions. Current use of a finger or surgical instrument is clumsy and obstructs the surgeon's view, whereas the minimally invasive applicator of the present invention provides a solution to a long-standing problem.

In addition, the applicator includes an ergonomically favorable hand grip, which acts to control the mechanism for wax delivery. The grip allows the surgeon the apply wax both quickly and in a controlled manner, using a single hand. The tip is optimized for the application because it allows for both controlled wax extrusion and precise application of wax to bone. The rounded tip allows the surgeon to push the wax into the proper place and spread it across cut bone surfaces.

While it is believed that the existing design effectively improves the current state of bone wax application, future work may be done to further optimize the device. For example, it is contemplated within the current invention that the applicator may be manufactured to be disposable and pre-loaded with sterile wax. In addition, battery/heating element combinations may be further optimized in order to achieve the desired wax temperature as quickly as possible and maintain it for as long as possible.

Reduction in the size of the battery to further reduce the weight of the device and further improve the surgeon's line of vision into the operative field is also envisioned. If the battery size is able to be reduced sufficiently, future versions of the device may feature a battery embedded within the grip or trigger assembly. To this end, the device may be fitted with a simple on/off switch.

In addition, the device may be made from a combination of a variety of materials including metals such as aluminum, plastics, or other materials in order to minimize the manufactured cost of the final commercially sold device.

Finally, it is important to note that this technology may be readily adapted to aid in the application of a number of other surgical materials used such as bone cement, resorbable biomaterials, or other wax-like materials all of which are embraced by the present invention.

The invention claimed is:

1. An apparatus for the application of a surgical material or substance at an elevated temperature, comprising:
    a) an applicator body, said body comprising: (i) a rear grip, (ii) a chamber for receiving said surgical material or substance, wherein the chamber for receiving surgical material or substance comprises a cover, wherein the chamber cover is a hatch, and (iii) a bayonet;
    b) a trigger assembly, pivotally actuable on the applicator body;
    c) an extrusion rod for engagement with said applicator body;
    d) a tip attached to the bayonet, wherein the tip comprises an angle of inclination of between 0-45 degrees relative to longitudinal axis of the bayonet; and
    e) a heating assembly for warming the surgical material or substance above room temperature, wherein the heating assembly comprises a heating element and a power source operably connected to said heating element, wherein the heating element is disposed about or along at least 10 percent of the length of the bayonet.

2. The apparatus of claim 1, wherein the surgical material or substance is selected from the group consisting of sealants, adhesives, therapeutic compositions, creams, ointments, gels, bone, hydroxyapatite and bone wax.

3. The apparatus of claim 1, wherein the bayonet is from between 10 cm and 30 cm in length and comprises internal diameter of between 0.1 cm and 1.0 cm and external diameter of between 0.5 and 1.5 cm.

4. The apparatus of claim 3, wherein the shape of the internal and external bayonet surfaces are the same.

5. The apparatus of claim 3, wherein the shape of the internal bayonet is round.

6. The apparatus of claim 3, wherein the shape of the external bayonet is a polygonal having between 3-8 sides.

7. The apparatus of claim 3, wherein the tip is formed by constriction of the terminus of the bayonet.

8. The apparatus of claim 7, wherein constriction produces a flattened surface and slit-like tip opening.

9. The apparatus of claim 1, wherein the tip is reversibly attached to the bayonet by means of a joint, hinge, slot, groove, whorl, screw, snap, or combinations thereof.

10. The apparatus of claim 1, wherein the hatch is hinged.

11. The apparatus of claim 1, wherein the hatch is slides over the chamber opening.

12. The apparatus of claim 1, wherein the applicator body further comprises a mounting platform.

13. The apparatus of claim 1, wherein the heating assembly comprises a heating element and a power source operably connected to said heating element.

14. The apparatus of claim 13, wherein the heating element is selected from the group consisting of a wire, a positive thermal coefficient (PTC) heating element and combinations thereof.

15. The apparatus of claim 14, wherein the heating element is a PTC heating element and the power source is selected from the group consisting of a battery and an external source operably tethered to the apparatus by a power cord.

16. The apparatus of claim 13, wherein the heating assembly further comprises one or more layers of insulation.

17. The apparatus of claim 16, wherein the insulation comprises a material selected from the group consisting of plastic, polyester film, polyethylene terephthalate, and combinations thereof.

18. The apparatus of claim 16, wherein the insulation is at least two layers of plastic disposed about the external surface of the heating element.

19. The apparatus of claim 18, further comprising at least one layer of heat shrink tubing disposed about the external surface of the insulation.

20. The apparatus of claim 1, wherein the trigger assembly comprises a front grip having a shaft for receiving a spring loaded hook, said spring loaded hook having a hook member for engaging the extrusion rod and a lever for disengaging said spring loaded hook, a grip attachment means disposed through a groove of the spring loaded hook for pivotally interconnecting the front grip to the applicator body, and a spring for supporting the spring loaded hook.

21. The apparatus of claim 1, wherein the extrusion rod comprises a first region and a
    second region, wherein said first region engages with the applicator body, the second region is notched about its external surface and engages with the trigger assembly.

22. The apparatus of claim 21, wherein the extrusion rod contains a third region juxtaposed to said second region and being is identical to said first region.

* * * * *